United States Patent [19]

Rehfuss

[11] Patent Number: 5,232,990
[45] Date of Patent: Aug. 3, 1993

[54] MELAMINE DERIVATIVE CROSS-LINKING AGENT

[75] Inventor: John W. Rehfuss, West Bloomfield, Mich.

[73] Assignee: BASF Corporation, Southfield, Mich.

[21] Appl. No.: 797,528

[22] Filed: Nov. 25, 1991

[51] Int. Cl.$^5$ ............................................. C08F 8/32
[52] U.S. Cl. .................................. 525/162; 525/327.3; 525/348; 525/349; 525/396; 528/375; 528/405; 528/406
[58] Field of Search ............... 525/162, 348, 349, 396; 528/375, 405, 406

[56] References Cited

U.S. PATENT DOCUMENTS

| | | | |
|---|---|---|---|
| 3,969,327 | 7/1976 | Stein et al. | 525/162 |
| 4,426,471 | 1/1984 | Berner | 525/162 |
| 4,515,835 | 5/1985 | Kuhn et al. | 525/162 |

*Primary Examiner*—Bernard Lipman
*Attorney, Agent, or Firm*—Paul L. Marshall

[57] ABSTRACT

Derivatives of melamine are disclosed having a carboxylic acid substituent on an amine nitrogen appended to the triazine ring. The compounds can be used to cross-link polymers having epoxy groups thereon.

12 Claims, No Drawings

MELAMINE DERIVATIVE CROSS-LINKING AGENT

FIELD OF THE INVENTION

This invention relates to a new compound that is useful in polymer chemistry, particularly as a cross-linking agent.

BACKGROUND OF THE INVENTION

Melamine is well-known as a cross-linking agent for polymers. Melamine, which is crystalline in its pure form, is typically reacted with formaldehyde and an alcohol to form an alkoxylated melamine resin. This resin can then be used as a cross-linking agent for a variety of polymers, such as hydroxyl group-containing polymers (e.g., hydroxyl acrylics, polyesters, hydroxyl urethanes). In this type of cross-linking reaction, the carbon atom that is alpha to the amino nitrogen on the melamine reacts with the hydroxyl group on the polymer in an acid-catalyzed reaction with the melamine's alkoxy substituent leaving as an alcohol.

Melamine resins have been used successfully as cross-linking agents for a variety of polymer systems, including hydroxyl acrylic polymer systems used in the automotive coatings area, and particularly for automotive clearcoats. They offer the advantage of being used in the so-called "one-pack" systems, where the cross-linkable coating composition can be coated as one formulation. However, when melamine cross-linked hydroxyl acrylic polymers are used in automotive clearcoat coatings, the resulting finish suffers from a phenomenon known as environmental etch. Environmental etch appears as milky or cloudy marks on clearcoat finishes that have been exposed to the elements.

There is thus a need in the art for a weather-resistant one-pack cross-linkable coating composition that uses a cross-linking agent other than the standard melamine aldehyde resin.

SUMMARY OF THE INVENTION

According to the present invention, cross-linking can be achieved with the use of a melamine derivative having a carboxylic acid substituent on an amine nitrogen appended to the triazine ring. Preferred melamine derivatives for use in the invention include compounds according to the formula:

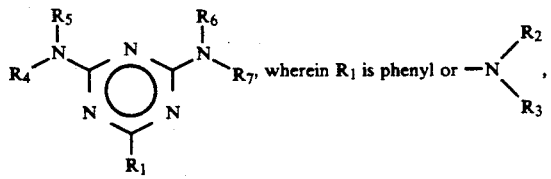

$R_2$, $R_3$, $R_4$, $R_5$, $R_6$, and $R_7$ are each independently —$CH_2OR$ or —$CH_2S$—L—$CO_2H$, with the proviso that at least one of $R_1$, $R_2$, $R_3$, $R_4$, $R_5$, and $R_6$ is —$CH_2S$—L—$CO_2H$, wherein R is alkyl, aryl, or cycloaliphatic, and L is a divalent organic linking group.

This compound can be used to cross-link polyepoxides. While the invention does not depend on the operation of any particular theory, it is believed that the cross-linking takes place via a ring-opening reaction between the carboxyl group on the melamine derivative and an epoxy ring on the polyepoxide. The cross-linked polymers thus produced are useful in a variety of applications, including automotive clearcoat. These polymers can also offer advantages such as good weatherability with low environmental etch, good hardness and scratch resistance, and good flexibility.

DESCRIPTION OF THE PREFERRED EMBODIMENTS

The melamine derivative used in the practice of the invention has at least one, and preferably at least two carboxylic acid substituent(s) on an amino nitrogen that is itself attached to the triazine ring. The carboxylic acid substituent comprises a carboxyl group and a linking moiety that links the carboxyl group with the amino nitrogen. Useful linking moieties can include a thioalkyl group, an amino acid (e.g., glycine) and a hydroxy acid (e.g., hydroxy acetic acid, hydroxy stearic acid). Preferred linking moieties are thioalkyl groups according to the formula —$CH_2S$—L— where L is a divalent organic linking group, preferably comprising 1 to 12 carbon atoms.

A preferred class of melamine derivatives useful in the present invention are those according to the formula:

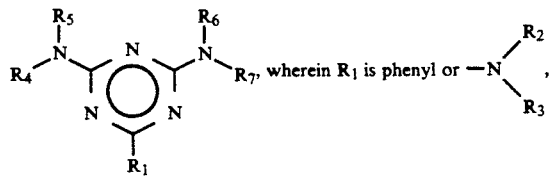

$R_2$, $R_3$, $R_4$, $R_5$, $R_6$, and $R_7$ are each independently —$CH_2OR$ or —$CH_2S$—L—$CO_2H$, with the proviso that at least one of $R_2$, $R_3$, $R_4$, $R_5$, $R_6$, and $R_7$ is —$CH_2S$—L—$CO_2H$, wherein R is alkyl, aryl, or cycloaliphatic, and L is a divalent organic linking group. Examples of R include substituted or unsubstituted alkyl, preferably of 1 to 8 carbon atoms (e.g., methyl, ethyl, n-propyl, n-butyl, i-butyl, 3-chloropropyl, benzyl), substituted or unsubstituted aryl, preferably of 6 to 20 carbon atoms (e.g., phenyl, naphthyl, 2-chlorophenyl, 4-chlorophenyl, 2-tolyl, 4-tolyl), and substituted or unsubstituted cycloaliphatic (e.g., cyclohexyl, cyclopentyl, isobornyl). Divalent organic linking groups used as L preferably comprise 1 to 12 carbon atoms in the linear chain between the S atom and the carboxyl group. Examples of L include saturated hydrocarbon linking groups (e.g., —$CH_2$—, —$CH_2CH_2CH_2$—, —$CH_2CHCH_2CH_2$—), hydrocarbon ether groups (e.g., —$CH_2CH_2$—O—$CH_2CH_2$—) divalent cycloaliphatic (e.g., cyclohexyl), divalent aromatic (e.g., phenyl).

The melamine derivative used in the present invention can be prepared by reacting melamine with an aldehyde and an alcohol to form an alkoxylated melamine, as is well-known in the art. The alkoxylated melamine can then be reacted with a mercaptocarboxylic acid (e.g., mercaptoproprionic acid, mercaptoacetic acid), an amino acid, or a hydroxy acid to displace the alkoxy groups, resulting in an acid-modified melamine, such as described in the formula above.

Among the polyepoxides that can be used are epoxy-containing acrylic polymers, which are preferred, epoxy condensation polymers such as polyglycidyl ethers of alcohols and phenols and certain polyepoxide monomers and oligomers. The epoxy-containing acrylic polymer is a copolymer of an ethylenically unsaturated monomer having at least one epoxy group and at least one polymerizable ethylenically unsaturated monomer that is free of epoxy groups.

Examples of ethylenically unsaturated monomers containing epoxy groups are those containing 1,2-epoxy groups and include glycidyl acrylate, glycidyl methacrylate, and allyl glycidyl ether.

Examples of ethylenically unsaturated monomers that do not contain epoxy groups are alkyl esters of acrylic and methacrylic acid containing from 1 to 20 atoms in the alkyl group. Specific examples of these acrylates and methacrylates are methyl methacrylate, ethyl methacrylate, butyl methacrylate, ethyl acrylate, butyl acrylate, and 2-ethylhexyl acrylate.

Examples of other copolymerizable ethylenically unsaturated monomers are vinyl aromatic compounds such as styrene and vinyl toluene, nitriles such as acrylonitrile and methacrylonitrile, vinyl and vinylidene halides such as vinyl chloride, and vinylidene fluoride and vinyl esters such as vinyl acetate. Acid group-containing copolymerizable ethylenically unsaturated monomers such as acrylic and methacrylic acid are preferably not used because of the possible reactivity of the epoxy and acid group.

The epoxy group-containing ethylenically unsaturated monomer is preferably used in amounts of from about 5 to 60, more preferably from 20 to 50 percent by weight of the total monomers used in preparing the epoxy-containing acrylic polymer. Of the remaining polymerizable ethylenically unsaturated monomers, preferably from 40 to 95 percent, more preferably from 50 to 80 percent by weight of the total monomers are the alkyl esters of acrylic and methacrylic acid.

In preparing the epoxy-containing acrylic polymer, the epoxide functional monomers and the other ethylenically unsaturated monomers can be mixed and reacted by conventional free radical initiated organic solution polymerization.

The epoxy-containing acrylic polymer typically has a number average molecular weight between about 1000 and 20,000, preferably 1000 to 10,000, more preferably 1000 to 5000. The molecular weight is determined by gel permeation chromatography using a polystyrene standard. In determining molecular weights in this fashion, it is not the actual molecular weights that are measured but an indication of the molecular weight as compared to polystyrene. The values that are obtained are commonly referred to as polystyrene numbers. However, for the purposes of this invention, they are referred to as molecular weights.

The epoxy condensation polymers that are used are polyepoxides, that is, those having a 1,2-epoxy equivalency greater than 1, preferably greater than 1 and up to about 3.0. Examples of such epoxides are polyglycidyl ethers of polyhydric phenols and of aliphatic alcohols. These polyepoxides can be produced by etherification of the polyhydric phenol or aliphatic alcohol with an epihalohydrin, such as epichlorohydrin, in the presence of alkali.

Examples of suitable polyphenols are 2,2-bis(4-hydroxyphenyl)propane (bisphenol A), 1,1-bis(4-hydroxyphenyl)ethane, and 2-methyl-1,1-bis(4-hydroxyphenyl)propane. Examples of suitable aliphatic alcohols are ethylene glycol, diethylene glycol, 1,2-propylene glycol, and 1,4-butylene glycol. Also, cycloaliphatic polyols such as 1,2-cyclohexanediol, 1,4-cyclohexanediol, 1,2-bis(hydroxymethyl)cyclohexane, and hydrogenated bisphenol A can also be used.

Besides the epoxy-containing polymers described above, certain polyepoxide monomers and oligomers can also be used. Examples of these materials are those containing the cyclohexane oxide moiety. These polyepoxides are of relatively low molecular weight and of relatively high reactivity, thus enabling the formation of high solids coating compositions with excellent cure response. The polyepoxides should have an average 1,2-epoxy equivalency of greater than one. The preferred polyepoxides are diepoxides, that is, having a 1,2-epoxy equivalency of two.

Various polyepoxides containing the cyclohexane oxide moiety are known. Particularly preferred in this regard is 3,4-epoxycyclohexylmethyl 3,4-epoxycyclohexane carboxylate. Also, the diepoxide bis(3,4-epoxy-6-methylcyclohexylmethyl) adipate can be used. These epoxides are commercially available from Union Carbide Corporation as ERL 4221 and ERL 4299, respectively. Also, epoxies containing the cyclohexane moiety are described in U.S. Pat. Nos. 2,890,194; 2,890,195; 2,890,196; 2,890,197; 2,890,210; 3,023,174; and 3,027,357.

Mixtures of polyepoxides, particularly mixtures of epoxy-containing acrylic polymers and polyepoxides containing a cyclohexane moiety, are preferred because they result in coating compositions that have high solids content and a good combination of coating properties, i.e., gloss, distinctness of image, adhesion, hardness and solvent resistance.

The polyepoxide is typically present in the liquid crosslinkable composition in amounts of 60 to 95, preferably from 65 to 80 percent by weight based on total weight of resin solids.

The equivalent ratio of the reactants present in the composition are preferably adjusted that for each equivalent of epoxy there are 0.5 to 1.5, preferably 0.8 to 1.2 equivalents of carboxyl.

The compositions will also preferably contain catalysts to accelerate the cure of the epoxy and carboxyl groups. Examples of suitable catalysts are basic materials and include organic amines and quaternary ammonium compounds such as pyridine, piperidine, dimethylaniline, diethylenetriamine, tetramethylammonium chloride, tetramethylammonium acetate, tetramethylbenzylammonium acetate, tetrabutylammonium fluoride, and tetrabutylammonium bromide. The amount of catalyst is typically from 0.1 to 10, preferably 0.5 to 3 percent by weight based on weight of resin solids.

Also, optional ingredients such as plasticizers, antioxidants, and UV light absorbers can be included in the composition. These ingredients typically may be present in amounts of up to 25 percent by weight based on total resin weight. For colored and/or textured coatings, pigments may be included in the compositions. Pigment contents in amounts of up to 75 percent by weight based on total solids can be used.

The compositions of the present invention are liquid compositions and are preferably formulated into liquid high solids coating compositions, that is, those coating compositions containing greater than 40, preferably greater than 55 percent by weight resin solids. The solids content is determined by formulating the coating composition to a No. 4 Ford cup viscosity of 25-30 seconds at 24° C.) and heating the composition to 105°-110° C. for 1 to 2 hours to drive off the volatile material.

The curable compositions of the invention can be applied as coatings to a substrate by any of the conventional coating techniques such as brushing, spraying, dipping or flowing, but it is preferred that spray applications be used since this gives the best appearance. Any of the known spray techniques may be employed such as compressed air spraying, airless spraying, electrostatic spraying and either manual or automatic methods.

After application of the coating composition to the substrate, the coated substrate is heated to cure the coating. In the curing operation, solvents are driven off and the film-forming material of the coating composition is crosslinked through reaction of the carboxyl groups and epoxy groups. The heating or curing operation is usually carried out at a temperature in the range of from 71°-177° C. The thickness of the coating is usually from about 0.1 to 5, preferably 0.1 to 3 mils.

Preferably, the compositions of the present invention, particularly those prepared with the aliphatic polyepoxides and with the epoxy-containing acrylic polymers, are used to formulate clear coats for use in a color-plus-clear application. In a color-plus-clear application, a composite coating is applied to a substrate. The process comprises applying to the substrate a pigmented or colored film-forming composition to form a base coat and applying to the base coat a second film-forming composition to form a transparent top coat over the base coat.

The film-forming composition of the base coat can be any of the compositions useful in coating applications, particularly automotive applications in which the color-plus-clear coating applications are finding their most use. A film-forming composition conventionally comprises a resinous binder and a pigment to act as a colorant. Particularly useful resinous binders are acrylic polymers, polyesters including alkyds, and polyurethanes.

The resinous binder for the base coat can be an organic solvent-based material such as those described in U.S. Pat. No. 4,220,679. Also, water-based coating compositions such as those described in U.S. Pat. No. 4,403,003 and U.S. Pat. No. 4,147,679 can also be used as the binder in the base coat composition. The resinous binder for the base coat can also be the curable composition of the present invention.

The base coat composition also contains pigments including metallic pigmentation to give it color. Examples of suitable pigmentations for the base coat are described in the aforementioned U.S. Pat. Nos. 4,220,679, 4,403,003, and 4,147,679.

Optional ingredients in the base coat composition are those which are well known in the art of formulating surface coatings and include surfactants, flow control agents, thixotropic agents, fillers, anti-gassing agents, organic co-solvents, catalysts and other customary auxiliaries. Examples of these materials and suitable amounts are described in the aforementioned U.S. Pat. Nos. 4,220,679, 4,403,003, and 4,147,679.

The base coat compositions can be applied to the substrate by any of the conventional coating techniques such as bruising, spraying, dipping or flowing, but they are most often applied by spraying. The usual spray techniques and equipment for air spraying, airless spraying and electrostatic spraying in either manual or automatic methods can be used.

During application of the base coat to the substrate, a film of the base coat is formed on the substrate typically in a thickness of about 0.1 to 5 and preferably about 0.1 to 2 mils.

After forming a film of the base coat on the substrate, solvent, that is, organic solvent and/or water, is driven out of the base coat film by heating or simply an air drying period before application of the clear coat. Preferably, the heating step will only be that sufficient and for a short period of time to insure that the clear top coat composition can be applied to the base coat without the former dissolving the base coating composition, that is, "striking in". Suitable drying conditions will depend on the particular base coat composition, on the ambient humidity with certain water-based compositions, but in general a drying time of from about 1 to 15 minutes at a temperature of 21°-79° C.) will be adequate to insure that mixing of the two coats is minimized. At the same time, the base coat film is adequately wetted by the clear top coat composition so that satisfactory intercoat adhesion can be obtained. Also, more than one base coat and more than one top coat may be applied to develop optimum appearance. Usually between coats, the previously applied base coat or top coat is flashed, that is, exposed to ambient conditions for about 1 to 20 minutes.

The clear top coat composition is applied to the base coat by any of the conventional coating techniques mentioned above, although spray applications are preferred. As mentioned above, the clear top coat is applied to the base coat via a wet-on-wet technique before the base coat has been cured. The two coatings are then heated to conjointly harden both coating layers. Curing conditions such as described above can be used. Clear coats typically have thicknesses of 0.5 to 5, usually 1 to 2.5 mils.

The invention is further described in the following Examples.

EXAMPLE 1

To a flask equipped with a vacuum distillation apparatus was added 1500 g Resimene® 755 melamine formaldehyde resin and 924 g mercaptoproprionic acid. The mixture was slowly heated to 70° C., and vacuum was applied. The vacuum was increased to 635 mm Hg, and the mixture was slowly heated to 90° C. When 279 g of the distillate (methanol) had been collected, the heating was discontinued and the vacuum removed. After the mixture had cooled, the acid-modified resin was filtered and collected.

EXAMPLE 2

The following components were combined in a mixing vessel under agitation:

| | |
|---|---|
| Poly(glycidyl methacrylate-co-hydroxyethyl methacrylate-co-ethylhexyl methacrylate-co-ethylhexyl acrylate-co-cyclo-hexyl methacrylate) [44.8/20.8/8.4/7.0/19.0] | 36.19 |
| Acid-modified resin from Example 1 | 9.04 |
| Tinuvin ® 123 (hindered amine) | 0.75 |
| Tinuvin ® 384 (UV absorber) | 1.50 |
| Aerosil ® R-972 (fumed silica) | 0.61 |
| Polybutyl acrylate | 0.35 |
| Amyl acetate | 29.90 |
| n-Butanol | 2.00 |
| Propylene glycol monoethyl ether acetate | 2.22 |

The glycidyl methacrylate-containing polymer was added at solids in the propylene glycol monoethyl ether acetate, and the acid-modified resin was added at 89% solids in the methylisobutyl ketone. The composition was mixed at ambient temperature for about 7 minutes, spray-coated as a layer about 45 μm thick onto a primed steel panel, and baked at 132° C. for 30 minutes to form an acid-resistant and solvent-resistant clearcoat finish.

The invention has been described in detail with reference to preferred embodiments thereof. It should be understood, however, that variations and modifications can be made within the spirit and scope of the invention.

I claim:

1. A method of cross-linking a polymer or prepolymer having at least one epoxy group with a melamine derivative having a carboxylic acid substituent on an amine nitrogen appended to the triazine ring, the method comprising reacting said epoxy group with said carboxylic acid substituent,
    said polymer or prepolymer being a polyglycidyl ether of a polyhydric phenol or aliphatic alcohol, or being derived from an acrylate or alkyl acrylate having an epoxy group attached thereto, and
    said melamine derivative having the formula:

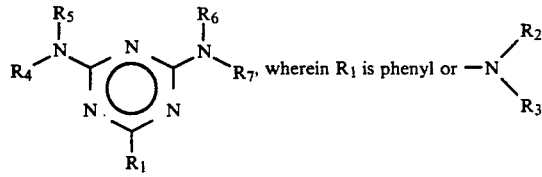

$R_2$, $R_3$, $R_4$, $R_5$, $R_6$, and $R_7$ are each independently —CH$_2$OR, —CH$_2$S—L—CO$_2$H, —CH$_2$O—L—CO$_2$H, or —CH$_2$—A—L—CO$_2$H, with the proviso that at least one of $R_2$, $R_3$, $R_4$, $R_5$, $R_6$, and $R_7$ is —CH$_2$S—L—CO$_2$H, —CH$_2$O—L—CO$_2$H, or —CH$_2$A—L—CO$_2$H, wherein R is alkyl, aryl, or cycloaliphatic, A is amino, and L is a divalent organic linking group.

2. A method according to claim 1 wherein the epoxy-containing polymer or prepolymer is derived from an acrylate or alkyl acrylate having an epoxy group attached thereto.

3. A method according to claim 1 wherein
    $R_2$, $R_3$, $R_4$, $R_5$, $R_6$, and $R_7$ are each independently —CH$_2$OR or —CH$_2$S—L—CO$_2$H, with the proviso that at least one of $R_2$, $R_3$, $R_4$, $R_5$, $R_6$, and $R_7$ is —CH$_2$S—L—CO$_2$H, wherein R is alkyl, aryl, or cycloaliphatic, and L is a divalent organic linking group.

4. A method according to claim 3 wherein L is —CH$_2$—.

5. A method according to claim 3 wherein L is —(CH$_2$)$_2$—.

6. A compound according to claim 3 wherein at least two of $R_1$, $R_2$, $R_3$, $R_4$, $R_5$, and $R_6$ are each independently —CH$_2$S—L—CO$_2$H.

7. A coating composition comprising:
    a polyepoxide that is a polyglycidyl ether of a polyhydric phenol or aliphatic alcohol, or is derived from an acrylate or alkyl acrylate having an epoxy group attached thereto, and
    a melamine derivative having a carboxylic acid substituent on an amine nitrogen appended to the triazine ring, according to the formula:

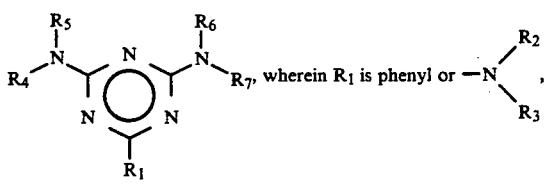

$R_2$, $R_3$, $R_4$, $R_5$, $R_6$, and $R_7$ are each independently —CH$_2$OR, —CH$_2$S—L—CO$_2$H, —CH$_2$O—L—CO$_2$H, or —CH$_2$—A—L—CO$_2$H, with the proviso that at least one of $R_2$, $R_3$, $R_4$, $R_5$, $R_6$, and $R_7$ is —CH$_2$S—L—CO$_2$H, —CH$_2$O—L—CO$_2$H, or —CH$_2$—A—L—CO$_2$H, wherein R is alkyl, aryl, or cycloaliphatic, A is amino, and L is a divalent organic linking group.

8. A coating composition according to claim 7 wherein the polyepoxide is an epoxy-containing acrylic polymer.

9. A coating composition according to claim 7 wherein
    $R_2$, $R_3$, $R_4$, $R_5$, $R_6$, and $R_7$ are each independently —CH$_2$OR, or —CH$_2$S—L—CO$_2$H, with the proviso that at least one of $R_2$, $R_3$, $R_4$, $R_5$, $R_6$, and $R_7$ is —CH$_2$S—L—CO$_2$H, wherein R is alkyl, aryl, or cycloaliphatic, and L is a divalent organic linking group.

10. A coating composition according to claim 9 wherein L is —CH$_2$—.

11. A coating composition according to claim 9 wherein L is —(CH$_2$)$_2$—.

12. A coating composition according to claim 9 wherein at least two of $R_1$, $R_2$, $R_3$, $R_4$, $R_5$, and $R_6$ are each independently —CH$_2$S—L—CO$_2$H.

* * * * *